United States Patent
Aguirre (10) Patent No.: US 11,944,404 B2
(45) Date of Patent: *Apr. 2, 2024

(54) SURGICAL DRAPE

(71) Applicant: Texas Mountain Group LLC, Colorado Springs, CO (US)

(72) Inventor: Javier Aguirre, Colorado Springs, CO (US)

(73) Assignee: Texas Mountain Group LLC, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/837,938

(22) Filed: Jun. 10, 2022

(65) Prior Publication Data

US 2022/0296325 A1 Sep. 22, 2022

Related U.S. Application Data

(63) Continuation of application No. 16/920,529, filed on Jul. 3, 2020, now Pat. No. 11,406,467.

(60) Provisional application No. 63/004,336, filed on Apr. 2, 2020.

(51) Int. Cl.
*A61B 46/00* (2016.01)
*A61B 17/42* (2006.01)
*A61B 46/20* (2016.01)
*A61M 1/00* (2006.01)

(52) U.S. Cl.
CPC .............. *A61B 46/40* (2016.02); *A61B 17/42* (2013.01); *A61B 46/20* (2016.02); *A61M 1/60* (2021.05); *A61B 2046/205* (2016.02)

(58) Field of Classification Search
CPC ... A61B 46/20; A61B 46/40; A61B 2046/205; A61B 17/42; A61M 1/0001
See application file for complete search history.

(56) References Cited

U.S. PATENT DOCUMENTS

| | | | | |
|---|---|---|---|---|
| 4,384,573 A | * | 5/1983 | Elliott | A61B 46/00 128/853 |
| 4,489,720 A | | 12/1984 | Morris et al. | |
| 4,616,642 A | | 10/1986 | Martin et al. | |
| 4,711,236 A | * | 12/1987 | Glassman | A61B 46/00 128/854 |
| 5,209,243 A | | 5/1993 | Glassman | |
| 5,464,024 A | | 11/1995 | Mills et al. | |

(Continued)

OTHER PUBLICATIONS

U.S. Appl. No. 63/004,336, filed Apr. 2, 2020.

(Continued)

*Primary Examiner* — Camtu T Nguyen
(74) *Attorney, Agent, or Firm* — Craig R. Miles; CR MILES P.C.

(57) ABSTRACT

A surgical drape adapted to overlay a patient including an opaque sheet having superior region extending to a cephalad end with a fenestration configured to surround a surgical region of the patient, and an inferior region extending from the inferior aspect of the fenestration to a caudal end and having a transparent sheet joined to the patient facing side of the opaque sheet proximate the inferior aspect of the fenestration between opposite opaque sheet first and second edges allowing the inferior portion of the opaque sheet drawn away from the transparent sheet to allow a surgeon visual access to the patient through the transparent sheet.

10 Claims, 11 Drawing Sheets

(56) References Cited

U.S. PATENT DOCUMENTS

| | | | | |
|---|---|---|---|---|
| 5,471,999 | A | 12/1995 | Mills | |
| 5,592,952 | A | 1/1997 | Bohn | |
| 7,610,918 | B2 * | 11/2009 | Bowen | A61B 46/30 128/853 |
| 7,770,583 | B2 * | 8/2010 | Harris | A61B 46/23 128/853 |
| 8,011,371 | B2 | 9/2011 | Rotolo | |
| 10,111,724 | B2 | 10/2018 | Schwartz et al. | |
| 10,188,474 | B2 | 1/2019 | Jarelle et al. | |
| 2003/0121522 | A1 * | 7/2003 | Gingles | A61B 46/00 128/853 |
| 2008/0006279 | A1 * | 1/2008 | Bodenham | A61B 46/00 128/853 |
| 2010/0192960 | A1 * | 8/2010 | Rotolo | A61B 46/00 128/854 |
| 2011/0252535 | A1 | 10/2011 | McNeil | |
| 2012/0222686 | A1 | 9/2012 | Lockwood et al. | |
| 2013/0112211 | A1 | 5/2013 | Power et al. | |
| 2015/0359596 | A1 | 12/2015 | Jarrelle et al. | |
| 2017/0014199 | A1 | 1/2017 | Schwartz et al. | |
| 2017/0258543 | A1 * | 9/2017 | Chua | A61B 46/40 |
| 2017/0265957 | A1 | 9/2017 | Chua et al. | |
| 2019/0142541 | A1 | 5/2019 | Neis et al. | |
| 2019/0216565 | A1 | 7/2019 | Menut et al. | |

OTHER PUBLICATIONS

U.S. Appl. No. 16/920,529, filed Jul. 3, 2020.
Cardinal Health. Cesarean Birth Drape, Clear Anesthesia Screen. Website, https://www.cardinalhealth.com/en/product-soulutions/medical/infection-control/surgical-gouwns/surgical-drapes/cesarean-birth-drape-clear-anesthesia-screen.html, originally downloaded Jul. 8, 2020, 3 pages.
Halyard Health. Obstetrics Drapes. Website, https://products.halyardhealth.com/surgical-solutions/surgical-drapes-packs-equipment-covers/surgical-drapes/obstetrics-drapes.html, originally downloaded Jul. 8, 2020, 20 pages.
Medline. Cesarean Section Surgical Drape with Pouch and Fenestration. Website, https://www.medline.com/product/Cesarean-Section-Surgical-Drape-with-Pouch-and-Fenestration/Obstetrics/Gynecology-Drapes/Z05-PF07160?question=&index=P1&indexCount=1, originally downloaded Jul. 8, 2020, 5 pages.
3M. 3M™ Steri-Drape™ Cesarean-Section Sheet with Incise Pouch 7965. Website, https://www.3m.com/3M/en_US/company-us/all-3m-products/~/3M-Steri-Drape-Cesarean-Section-Sheet-with-Incise-Pouch-7965/?N=5002385+3294795901&rt=rud, originally downloaded Jul. 8, 2020, 1 page.
PCT International Patent Application No. PCT/US21/22829, International Search Report and Written Opinion of the International Searching Authority dated Jun. 8, 2021, 13 pages.
Corresponding Canadian Patent Application No. 3,171,856, Office Action dated Nov. 23, 2023, 4 pages.

* cited by examiner

SURGICAL DRAPE

This United States patent application is a continuation of U.S. patent application Ser. No. 16/920,529, filed Jul. 3, 2020, which claims the benefit of U.S. Provisional Patent Application No. 63/004,336, filed Apr. 2, 2020, each hereby incorporated by reference herein.

I. FIELD OF THE INVENTION

A surgical drape adapted to overlay a patient including an opaque sheet having superior region extending to a cephalad end with a fenestration configured to surround a surgical region of the patient, and an inferior region extending from the inferior aspect of the fenestration to a caudal end and having a transparent sheet joined to the patient facing side of the opaque sheet proximate the inferior aspect of the fenestration between opposite opaque sheet first and second edges allowing the inferior portion of the opaque sheet to be drawn away from the transparent sheet to allow a surgeon visual access to the patient through the transparent sheet.

II. SUMMARY OF THE INVENTION

There would be a substantial advantage in an inventive surgical drape including a transparent sheet joined to the patient facing side of an opaque sheet proximate the inferior aspect of the fenestration to allow the inferior portion of the opaque sheet to be drawn away from the transparent sheet overlaying the patient to allow a surgeon visual access to the patient during a surgical procedure. In particular, during a cesarean section during which the risk of obstetrical hemorrhage can be high, the opaque sheet can be drawn away from the transparent sheet to allow visual access to the vaginal region of a patient during the cesarean section to identify and to take remedial measures in view of obstetrical hemorrhage during the cesarean section.

Accordingly, broad object of the invention can be to provide a surgical drape including at least one or more of an opaque sheet having a surgeon facing side and a patient facing side extending to opposite opaque sheet side ends and opposite opaque sheet caudal and cephalad ends, the opaque sheet including a superior region having a fenestration portion to allow a surgeon access to a surgical region of a patient, and can include a screen portion to occlude patient's visual access to a surgical region when the opaque sheet overlays the patient, and an inferior region having a transparent sheet joined by a peripheral margin to the patient facing side of the opaque sheet proximate the fenestration allowing when overlaying a patient to move the inferior portion of the opaque sheet in relation to the transparent sheet to allow a surgeon visual access to a patient through the transparent sheet.

Another broad object of the invention can be a method of making a surgical drape at least including obtaining an opaque sheet having a surgeon facing side and a patient facing side extending to opposite opaque sheet side ends and opposite opaque sheet caudal and cephalad ends, the opaque sheet including a superior region having a fenestration portion adapted to surround a surgical region of a patient when the opaque sheet overlays the patient, and an inferior region extending from the inferior aspect of the fenestration to the caudal end, and joining a peripheral margin of a transparent sheet to the patient facing side of the opaque sheet proximate the inferior aspect of the fenestration and extending between or beyond opposite opaque sheet side ends and extending to or beyond the caudal end of the opaque sheet, the inferior region of the opaque sheet movable in relation to the transparent sheet when the surgical drape overlays the patient.

Another broad object of the invention can be a method of using a surgical drape at least including overlaying a patient with a surgical drape having a transparent sheet joined to the patient facing side of an opaque sheet proximate the inferior aspect of a fenestration and positioning the fenestration to surround the surgical region of the patient. The method further including moving the opaque sheet in relation to the transparent sheet overlaying the patient to allow a surgeon visual access to a patient through the transparent sheet.

Naturally, further objects of the invention are disclosed throughout other areas of the specification, drawings, photographs, and claims.

IV. DETAILED DESCRIPTION OF THE PREFERRED EMBODIMENTS

Now, with general reference to FIGS. 1A and 1B through 4 and 5A through 5E, embodiments of a surgical drape (1) can include an opaque sheet (2) having a surgeon facing side (3) opposite a patient facing side (4) extending to an opaque sheet first side edge (5) opposite an opaque sheet second side edge (6) and an opaque sheet caudal edge (7) and an opaque sheet cephalad edge (8). Any suitable surgical drape material (9) or combination of surgical drape materials can be used in the structure of the surgical drape (1) including as illustrative examples: plastic, polyethylene, polypropylene, spunbond polypropylene, meltblown polypropylene, spunlace polypropylene, and combinations thereof, such as laminates including two, three, four, five or more layers of the foregoing materials in various combinations.

A superior region (10) of the opaque sheet (2) when overlaying the patient (11) extends from about a patient's waist (12) toward a patient's head (13). The superior region (10) of the opaque sheet (2) can, but need not necessarily, include one or more of a fenestration portion (15) including a fenestration (16) to allow a surgeon to access a surgical region (17) of a patient (11) when the opaque sheet (2) overlays the patient (11), and in particular embodiments a screen portion (18) which can be positioned to occlude patient's (11) visual access to the surgical region (17). An inferior region (19) of the opaque sheet (2) when overlaying the patient (11) extends from proximate the inferior aspect of the fenestration (16) toward the patient's feet (14). In particular embodiments, the opaque sheet caudal edge (7) be disposed proximate, at, or beyond the patient's feet (14).

In particular embodiments, a transparent sheet (20) can overlay the patient facing side (4) of the opaque sheet (2). The transparent sheet (20) having surgeon facing side (78) and a patient facing side (79) extending between a transparent sheet first side edge (21) opposite a transparent sheet second side edge (22) and transparent sheet first end edge (23) and a transparent sheet second end edge (24) can have a transparent sheet edge margin (25) joined to the patient facing side (4) of the opaque sheet (2) proximate the fenestration (16) between opaque sheet first and second side edges (5)(6) to allow the inferior region (19) of the patient facing side (4) of the opaque sheet (2) to be in coextensive separable contact with the transparent sheet (20). In particular embodiments, the transparent sheet may extend beyond one or more of the opaque sheet first and second side edges (5)(6) or the opaque sheet caudal edge (7). The inferior region (19) of the opaque sheet (2) can be moved in relationship to the transparent sheet (20) (as shown in the illustrative examples of FIG. 1A or 1B and 2, whether drawn, rolled, or folded away from the transparent sheet (20)) to allow a surgeon (not depicted) visual access to the patient (11) through the transparent sheet (20). Any suitable transparent or substantially transparent material (26) or combination of materials can be used in the structure of the transparent sheet (20), including as illustrative examples, plastic, polyethylene, polypropylene, polyvinylchloride, nylon, and combinations thereof such as laminates including two, three, four, five or more layers of the foregoing materials in various combinations; provided that the material remains sufficiently transparent through which to view the patient (11).

In particular embodiments, the transparent sheet edge margin (25) can, but need not necessarily be inseparable joined to the patient facing side (4) of the opaque sheet (2). As illustrative examples, the transparent sheet edge margin (25) can be inseparable joined by one or more adhesion element(s) (27) such as: heat weld, thermal strip weld, hot air weld, double sided adhesive tape, adhesive layer, pressure sensitive adhesive, spray adhesive, urethane adhesive, silicone adhesive, epoxy adhesive, or combinations thereof.

In particular embodiments, the transparent sheet edge margin (25) can, but need not necessarily be separably joined to the patient facing side (4) of the opaque sheet (2). As illustrative examples, the transparent sheet edge margin (25) can be separable joined by a transparent sheet excision element (28), as illustrative examples, one or more of: perforated or non-perforated tear lines disposed along the transparent sheet edge margin which allows the transparent sheet to be separated in whole or in part from the opaque sheet (2).

In particular embodiments, the inferior region (19) of the opaque sheet (2) can, but need not necessarily be, separably joined to the surgeon facing side (78) of the transparent sheet (20) proximate the caudal aspect of the fenestration (16). As illustrative examples, the inferior region (19) of the opaque sheet (2) can be separable joined to the transparent sheet (20) by an opaque sheet adhesion element (71) disposed on patient facing side (4) of the opaque sheet (2) between opaque sheet first and second side edges (5)(6) proximate caudal aspect of the fenestration (16). As an illustrative example, the opaque sheet adhesion element (71) can comprise a removable and repositionable adhesive layer (72) disposed on the opaque sheet (2) or the transparent sheet (20) allowing the inferior region (19) of the opaque sheet (2) to be removed from the surgical drape (1) and later repositioned over the transparent sheet (20).

In particular embodiments, the inferior region (19) of the opaque sheet (2) can, but need not necessarily, include an opening (73) communicating between the surgeon facing side (3) and the patient facing side (4) and disposed medially and proximate the caudal aspect of the fenestration (16) to allow visual access to the vaginal region (70) of the patient (11). In particular embodiments, the surgical drape can, but need not necessarily, include a movable panel (74) overlaying the opening (73) to occlude visual access to the vaginal region (70). As shown in the illustrative example of FIG. 1A, the movable panel (74) can be entirely separate from the opaque sheet (2) or can have a panel edge (75) joined to the opaque sheet (2) to allow hinged movement of the movable panel (74) between a closed condition and an open condition to allow visual access to the vaginal region (70).

In particular embodiments, the transparent sheet (20) can be retrofit to a conventional opaque sheet (2) by providing transparent sheet edge margin adhesive layer (29) on the transparent sheet edge margin (25) with an overlaying transparent sheet edge margin peelable layer (30). The transparent sheet edge margin peelable layer (30) can be peeled from the transparent sheet edge margin adhesive layer (29) and the transparent sheet edge margin (25) adhesively joined to the patient facing side (4) of the opaque sheet (2) proximate the fenestration (16) between opaque sheet first and second side edges (5)(6).

In particular embodiments, one or more grippable elements (31) can be coupled to the surgeon facing side (3) of said opaque sheet (2) to allow ready grasp of the inferior region (19) of the opaque sheet (2). The one or more grippable elements (31) can, but need not necessarily, be disposed medially between opposite opaque sheet first and second side edges (5)(6) proximate the opaque sheet caudal edge (7). The grippable elements (31) can, but need not necessarily, be in the form of one or more of: loops, strings, cords, wires, flaps, or tabs, or other extending element, having a grip first end (32) coupled to the opaque sheet (2) and extending outward to an unattached grip second end (33).

In particular embodiments, the fenestration (16) can have a fenestration peripheral margin (34) having an overlaying fenestration peripheral margin adhesive layer (35) on the patient facing side (4) of said opaque sheet (2). A fenestration peripheral margin peelable layer (36) can be disposed over the fenestration peripheral margin adhesive layer (35) of opaque sheet (2). The fenestration peripheral margin peelable layer (36) can be peeled from the fenestration peripheral margin adhesive layer (35) and the fenestration peripheral margin adhesive layer (35) adhered to the patient (11) to locate the surgical region (17) within the fenestration (16) of the opaque sheet (2).

In particular embodiments, the opaque sheet (2) can, but need not necessarily, include a transparent incision film (37) which can be separate from the opaque sheet (2) and adhered to the patient (11) prior to overlaying the patient (11) with the opaque sheet (2), or joined to the opaque sheet (2) overlaying the open area of the fenestration (16) in the opaque sheet (2). In particular embodiments, the transparent incision film (37) can be joined to the patient facing side (4) of the opaque sheet (2) by an incision sheet adhesion element (38) including one or more of: heat weld, thermal strip weld, hot air weld, double sided adhesive tape, adhesive layer, pressure sensitive adhesive, spray adhesive, urethane adhesive, silicone adhesive, epoxy adhesive, or combinations thereof. The transparent incision film (37) can be disposed over the surgical region (17) when the opaque sheet (2) overlays the patient (11). In particular embodiments, the transparent incision film (37) can, but need not necessarily, further include an incision film adhesive layer (39) covering the patient facing side (4) of the transparent incision film (37) or applied to the transparent incision film margin (40). In particular embodiments, the incision film adhesive layer (39) can comprise the external surface of the transparent incision film (37) which may be self-adhering to the patient (11). When the surgical drape (1) overlays the patient, the incision film adhesive layer (39) can be covered by a peelable backing (41). When the procedure is performed, the peelable backing (41) can be peeled from the incision film adhesive layer (39). The incision film adhesive layer (39) can be adhered to the patient (11) around or over the surgical region (17). When the surgical procedure is performed, incisions may be made directly through the transparent incision film (37). The transparent incision film (37) can comprise any suitable substantially transparent or transparent material, and as an illustrative example the transparent incision film can comprise one or more of: a polyethylene film, polypropylene, polystyrene, nylon, or combinations thereof.

In particular embodiments, a fluid collecting pouch (42) can, but need not necessarily, be affixed to or around the transparent incision panel (37) or the surgeon facing side (3) of said opaque sheet (2) to collect bodily fluids (50) during the surgical procedure. The fluid collecting pouch (42) includes a pouch inner wall (43) opposite a pouch outer wall (44) joined at pouch outer perimeter (45) and extending to a collecting pouch inner perimeter (46) disposed around the surgical region (17). In particular embodiments, the inner perimeter margin (46) of the pouch inner wall (43) can be inseparably joined or separable joined to the surgeon facing side (3) of the opaque sheet (2) or the transparent incision panel (37) by a pouch adhesion element (47) by one or more of: heat weld, thermal strip weld, hot air weld, double sided adhesive tape, adhesive layer, pressure sensitive adhesive, spray adhesive, urethane adhesive, silicone adhesive, epoxy adhesive. The fluid collecting pouch (42) can be structured from any suitable material compatible with the bodily fluids of the patient (11) and can be a substantially transparent or transparent material such as: plastic, polyethylene, polypropylene, polyvinylchloride, nylon, and combinations thereof. In particular embodiments, a malleable material (48) can be disposed along all or a part of the pouch inner wall (43) or outer wall (44) inner perimeter margin (49). The malleable material (48) can be configured to position and conform the collection pouch inner perimeter (46) around the surgical region (17) or manipulation of the fluid collecting pouch (42) into the pouch open condition (51) to collect bodily fluids (50). In particular embodiments, one or more pouch gripping elements (52) can be coupled to the fluid collecting pouch (42) to allow ready grasp of the fluid collecting pouch (42) for positioning about the fenestration (16) or surgical region (17). The one or more pouch gripping elements (52) can, but need not necessarily, be disposed proximate the cephalad portion of the collecting pouch outer perimeter (45). The pouch gripping elements (52) can, but need not necessarily, be in the form of one or more of loops, strings, cords, wires, flaps, or tabs having a pouch gripping element first end (53) coupled to the pouch outer wall (44) and extending outward to a pouch gripping element unattached end (54). The fluid collecting pouch (42) can, but need not necessarily, include a fluid port (55) through which bodily fluid (50) can be conducted away from the fluid collecting pouch (42). The fluid port (55) can, but need not necessarily, include a port valve (56) or a port closure (57) operable to close the fluid port (55) to the egress of bodily fluid (50). In particular embodiments, the fluid port (55) can be configured to mate directly or indirectly with an aspirator (58) operable to generate a vacuum to draw bodily fluids (50) from the fluid collecting pouch (42) to a fluid collection container (59).

In particular embodiments, an absorbent pad (60) can be separably or inseparably coupled to the surgeon facing side (3) of the opaque sheet (2) medially between opaque sheet first and second side edges (5)(6) and caudal to the inferior aspect of the fluid collecting pouch outer perimeter (45). The absorbent pad (60) can comprise any suitable material for absorption of bodily fluids (50) from the surgical region (17). The absorbent pad material (61) can comprise as illustrative examples, one or more of: cellulose, cotton, linen, dry-laid cellulose-vinyl acetate, blown polyethylene or polypropylene microfibers, paper, spunbond polypropylene, meltblown polypropylene, spunlace polypropylene, or combinations thereof. The absorbent pad (60) may also include an impervious liner between the absorbent pad (60) and the surgeon facing side (3) of the opaque sheet (2)

In particular embodiments, anchors (76) can be attached to the surgeon facing side (3) of the opaque sheet (2). The anchors (76) can be have various configurations and locations to correspondingly hold various anchorable objects or materials such as instruments, tools, tubing, wires, devices or the like. While the embodiment of the anchors (76) shown in the Figures include outwardly extending tabs having one or more anchor apertures (77) to retain anchorable objects or materials; this is not intended to preclude embodiments which hold the anchorable objects or materials by other structural forms such as hook and loop, magnets, hooks, rings, loops, snaps, or the like.

The surgical drape (1) in whole or in part can be provided in a sterile condition (62). In particular embodiments, the transparent sheet (20) joined to the opaque sheet (2) can be provided in a sterile condition (62). As an illustrative example, the surgeon facing side (78) of the transparent sheet (20) can include a transparent sheet sterile center portion (63) which only correspondingly contacts an opaque sheet sterile center portion (64) on the patient facing side (4) of the opaque sheet (2). Therefore, the inferior region (19) of the opaque sheet (2) can be moved to expose the transparent sheet (20) with no or a reduced risk of contamination. The surgical drape (1) in the sterile condition (62) can be disposed in a folded condition (65) to dispose as an outside layer (66) of the folded condition (65) the fenestration (16) on the patient facing side (4) of the opaque sheet (2). The fenestration peripheral margin peelable layer (36) over the fenestration peripheral margin adhesive layer (35) disposed around the fenestration (16) can be peeled away to expose the fenestration peripheral margin adhesive layer (35) which can be adhered to the patient (11) with the fenestration (16) surrounding the surgical region (17). The surgical drape (1) can then be unfolded to overlay the patient (11).

Now, with primary reference to FIGS. 1A, 1B, 2 and 6, a method of using embodiments of the inventive surgical drape (1) can include one or more of: placing a patient (11) on an operating table (67) in supine position (block S1). Removing the surgical drape (1) from a packaging material (68) and handing the surgical drape (1) to the surgical team in typical sterile fashion while wrapped in a sterile covering (69) (block S2). Removing the sterile covering (69) (S3), and while the surgical drape (1) remains in a folded condition (65) or when overlaying the patient (11), removing a peelable layer (36) from the adhesive layer (35) disposed around the fenestration (16)(block S4). As to those embodiments including a transparent incision film (37), the method can include removing the peelable backing (41) from the incision film adhesive layer (39) disposed on the transparent incision film (37) or the transparent incision film margin (40)(block S5). Aligning the fenestration (16) around the surgical region (17) of the patient (11)(block S6). Adhering the adhesive layer (35)(39) disposed around the fenestration (16) or the transparent incision film (37) to the patient (11)(block S7). The method can further include, unfolding the surgical drape (1) in both the caudal and cephalad directions from the surgical region (17) to overlay the patient (11)(block S8). Supporting a screen portion (18) of the surgical drape (1) to occlude the patient's (11) visual access to the surgical region (17)(block S9). In particular embodiments, in which the surgical drape (1) includes an opaque sheet (2) and an underlaying transparent sheet (20) joined to the patient facing side (4) of the opaque sheet (2), unfolding can further include unfolding the surgical drape (1) in both the caudal and cephalad directions from the surgical region (17) to overlay the patient (11) with the transparent sheet (20) overlaying the patient (11) from about the patient's waist (12) toward the patient's feet (14) (block S10).

Figure 1A:
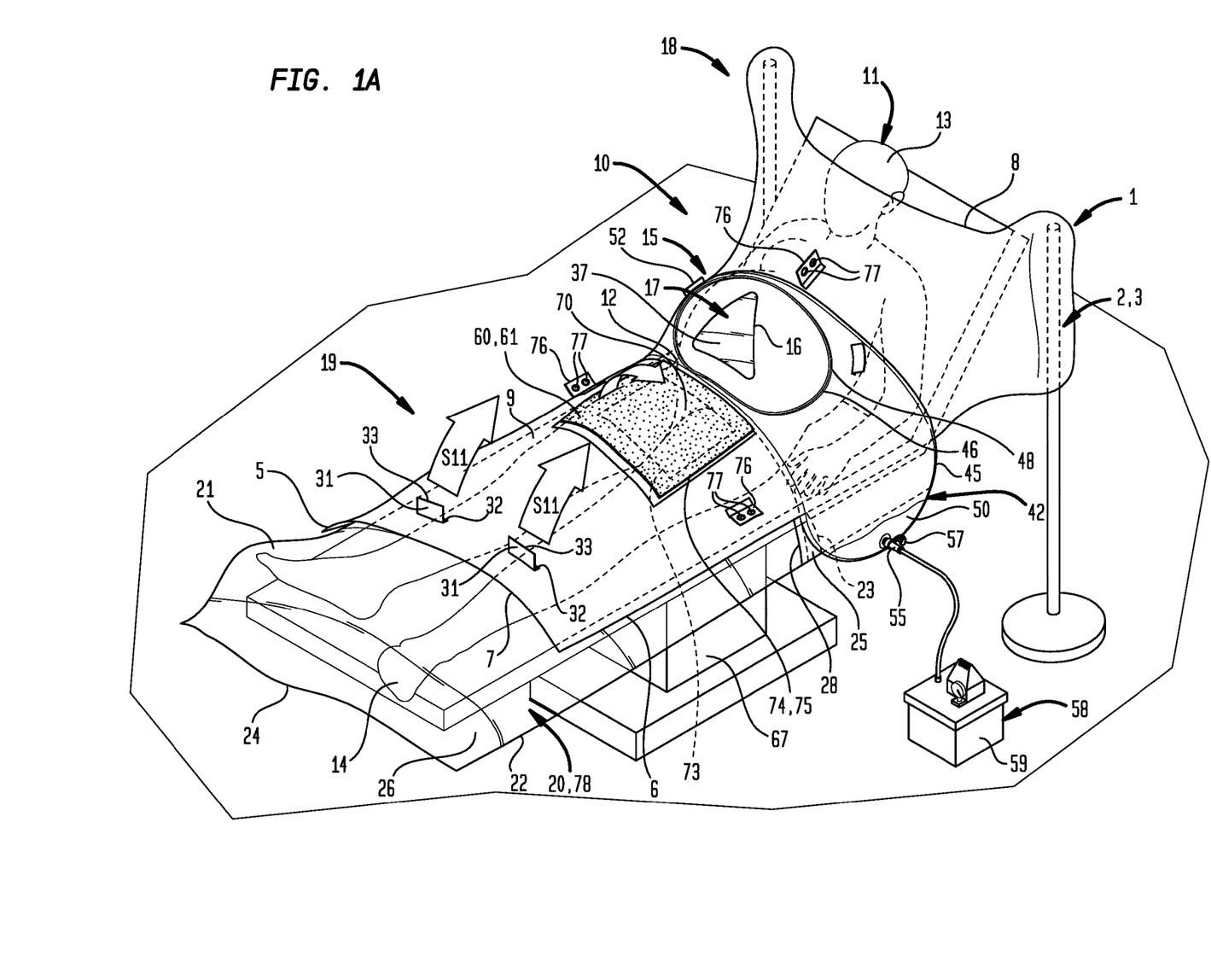
FIG. 1A is an illustration of an embodiment of the inventive surgical drape and a method of overlaying a patient with the surgical drape.
Figure 1B:
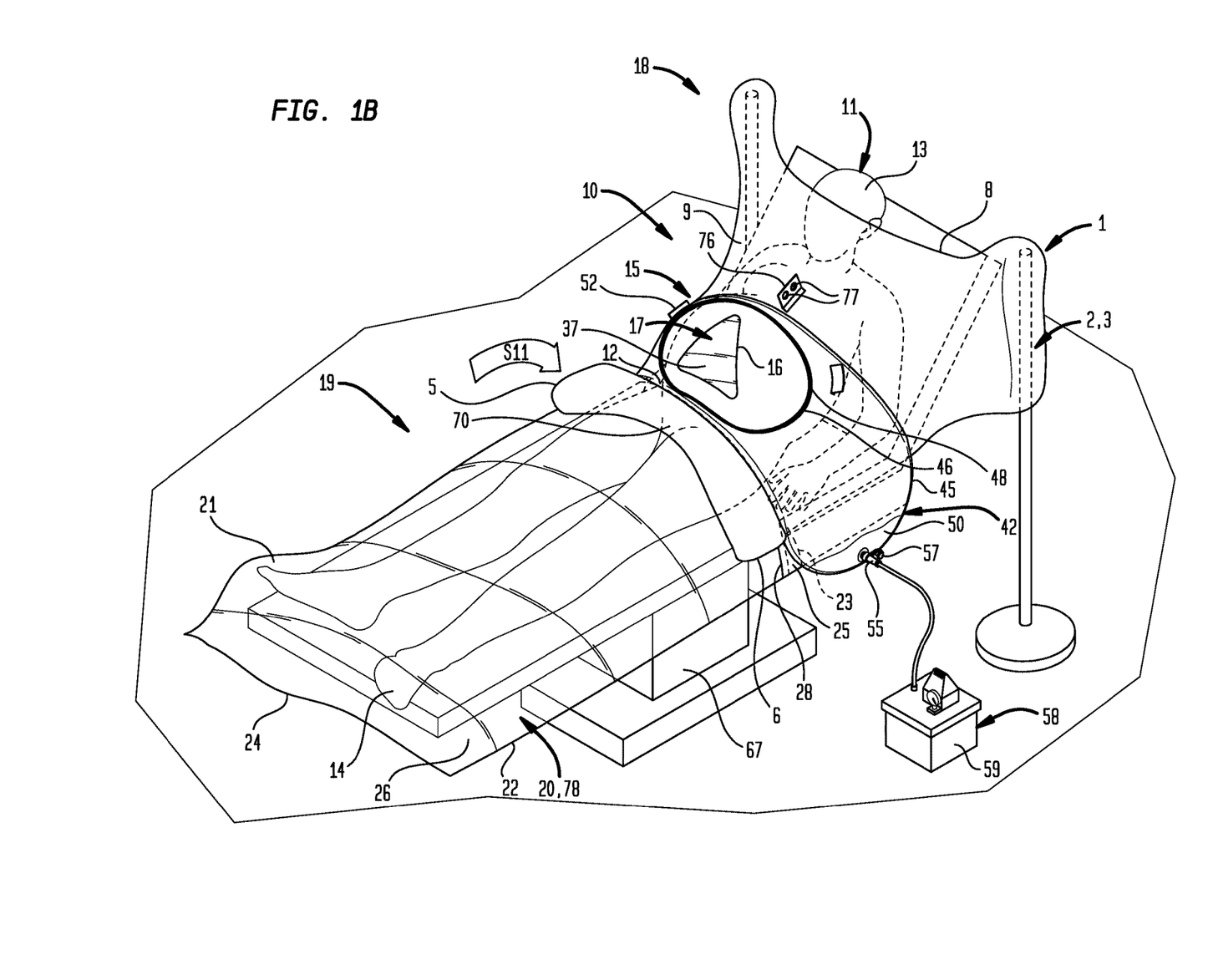
FIG. 1B is an illustration of the embodiment of the inventive drape depicted in FIG. 1A and a method of moving an inferior portion of an opaque sheet of surgical drape away from the underlying transparent sheet to visualize the patient.
Figure 2:
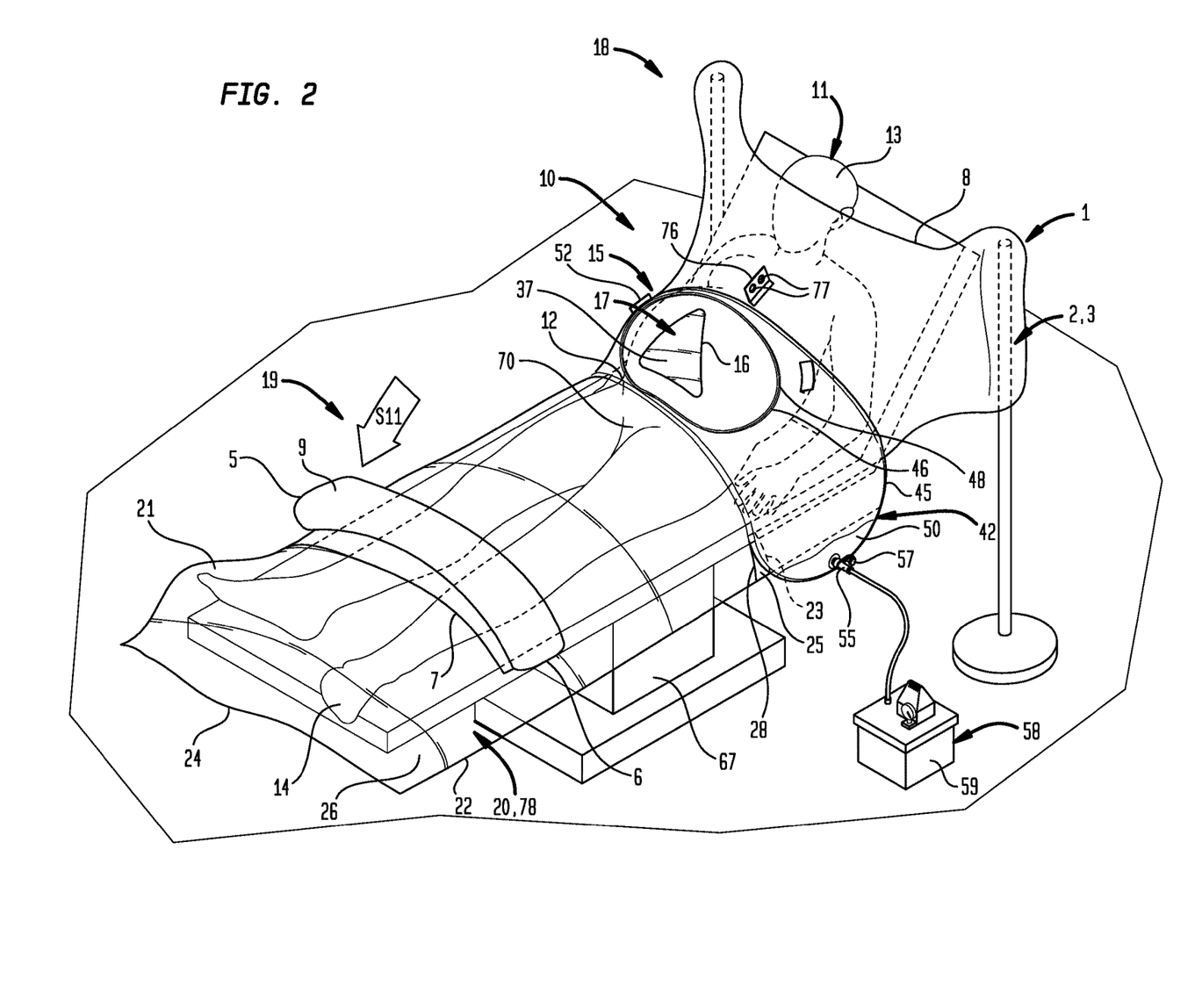
FIG. 2 is an illustration of the embodiment of the inventive drape depicted in FIG. 1A and an alternate method of moving an inferior portion of an opaque sheet of surgical drape away from the underlying transparent sheet to visualize the patient.
Figure 3:
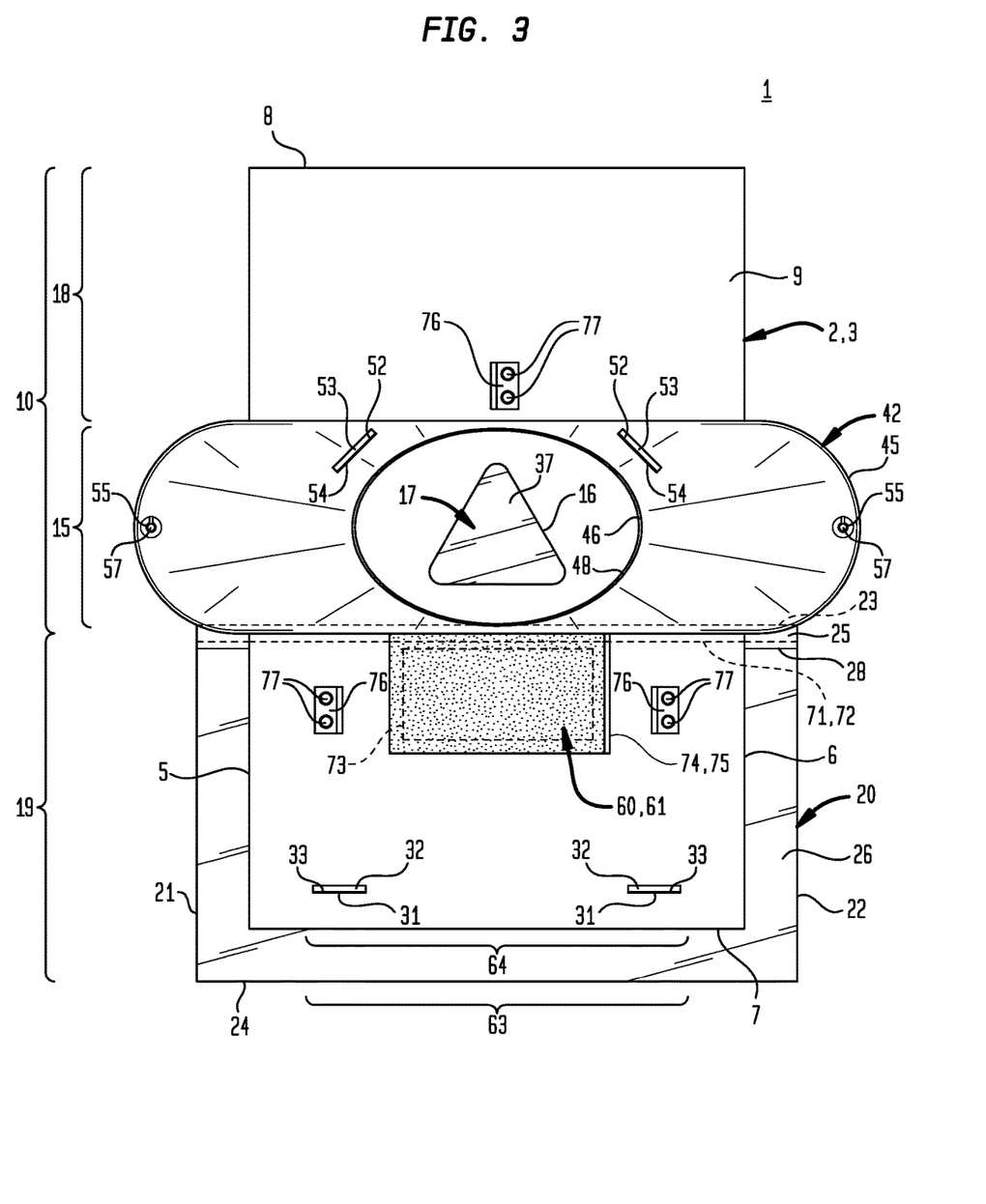
FIG. 3 is a surgeon facing plan view of an embodiment of the inventive surgical drape.
Figure 4:
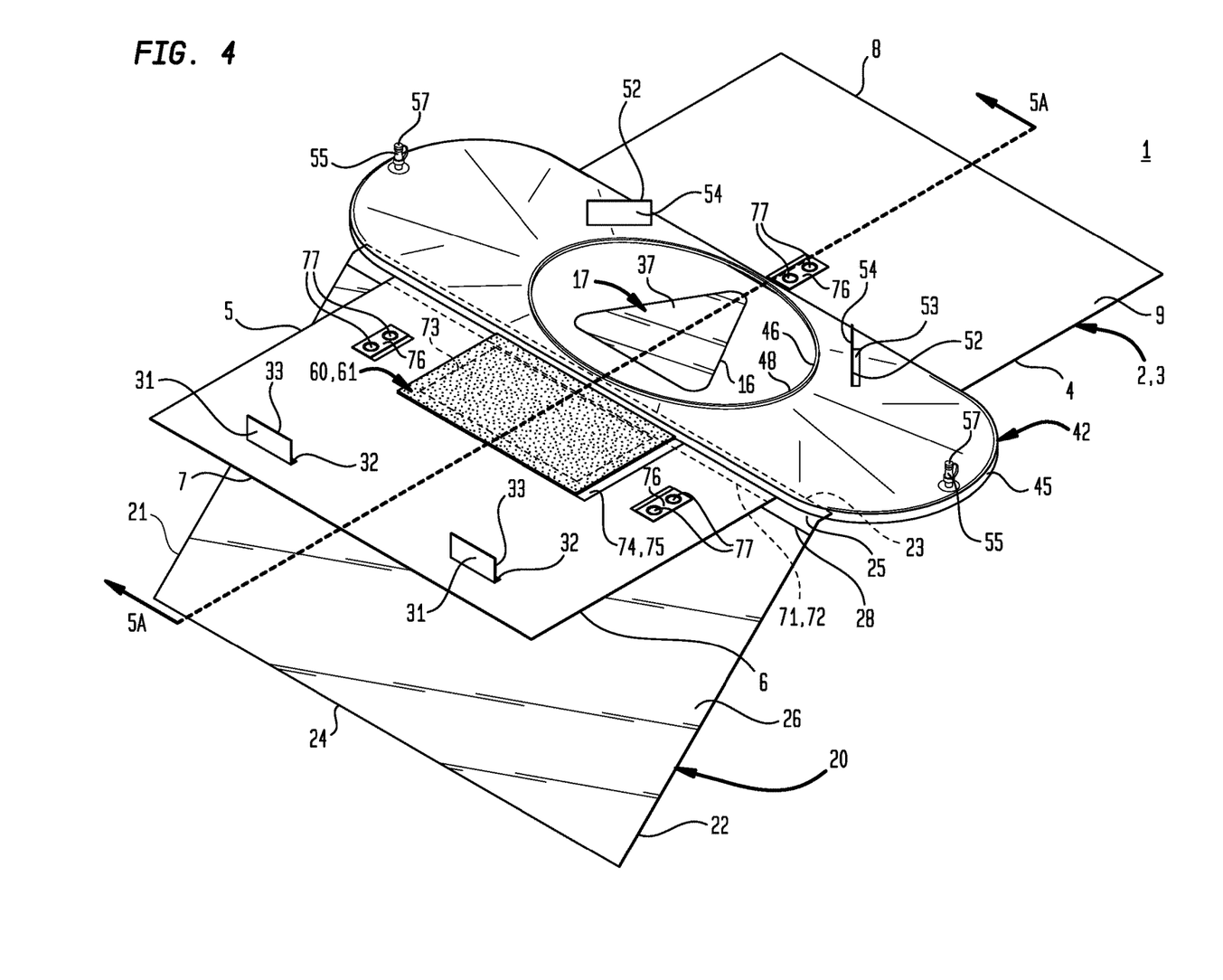
FIG. 4 is a perspective view of an embodiment of the inventive surgical drape having the inferior region of the opaque sheet of the surgical drape spaced apart from the transparent sheet of the surgical drape.
Figure 5A:
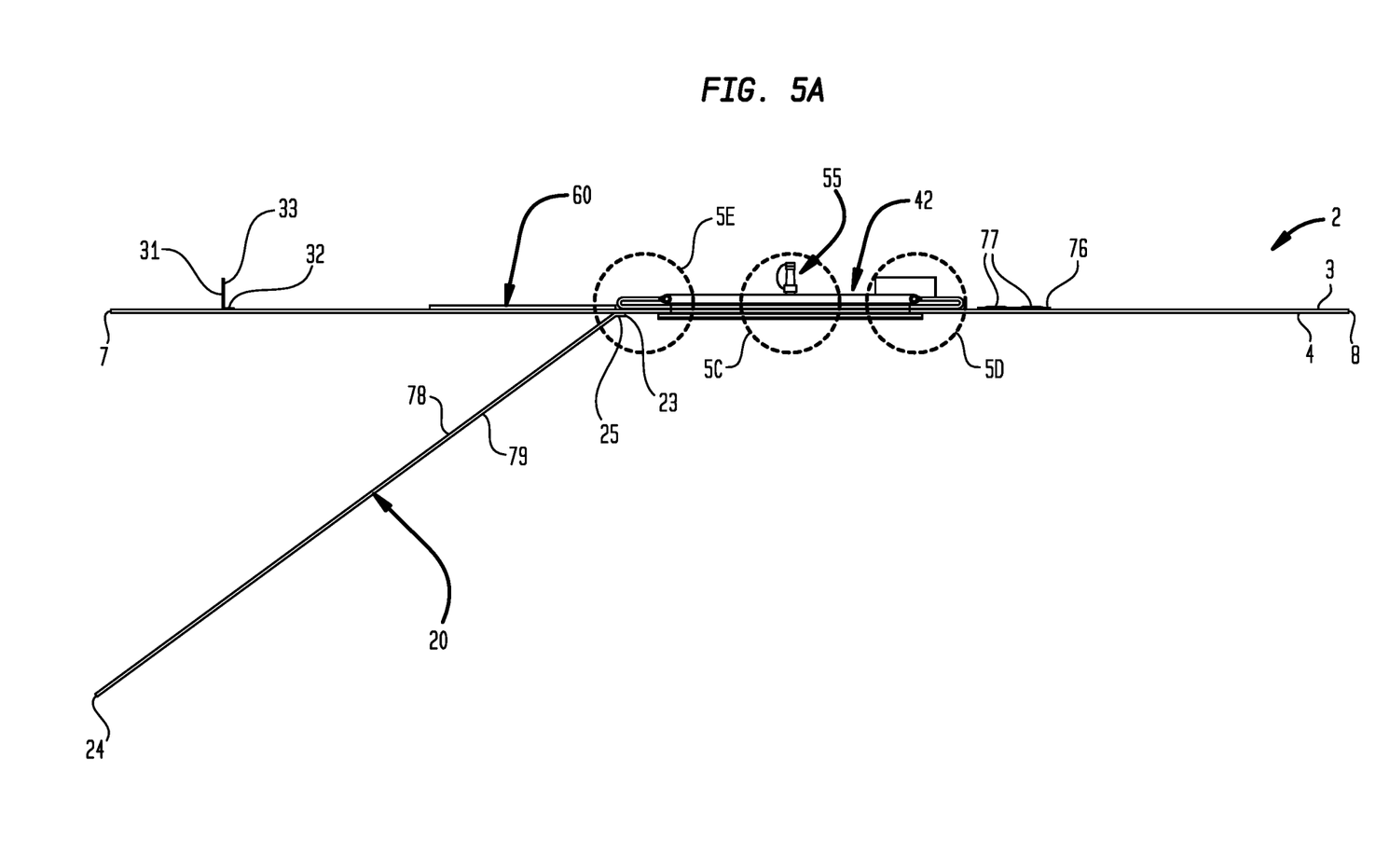
FIG. 5A is cross section 5A-5A of the embodiment of the surgical drape depicted in FIG. 4.
Figure 5B:
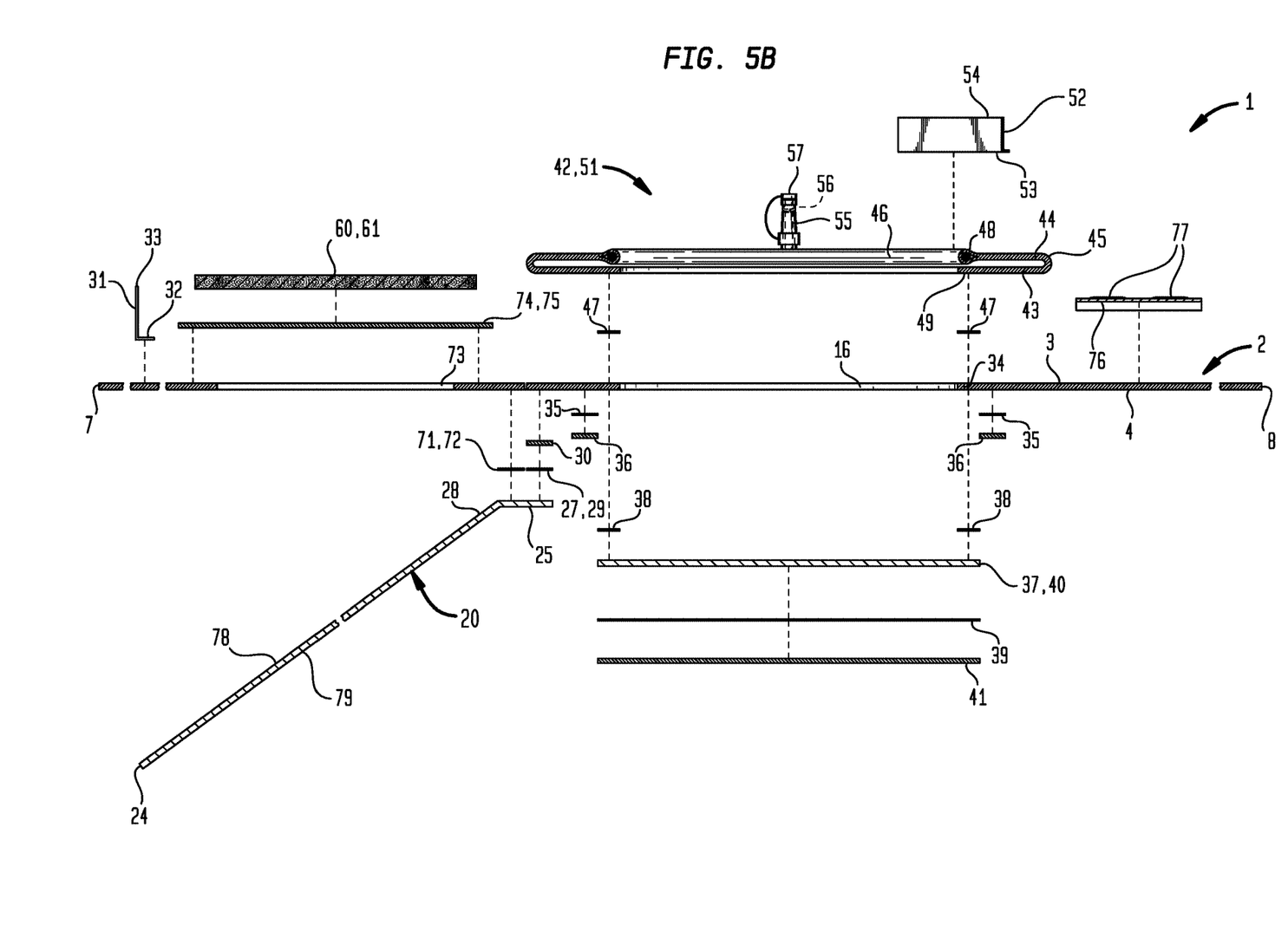
FIG. 5B is an exploded view of the embodiment of the surgical drape depicted in FIG. 5A.
Figure 5C:
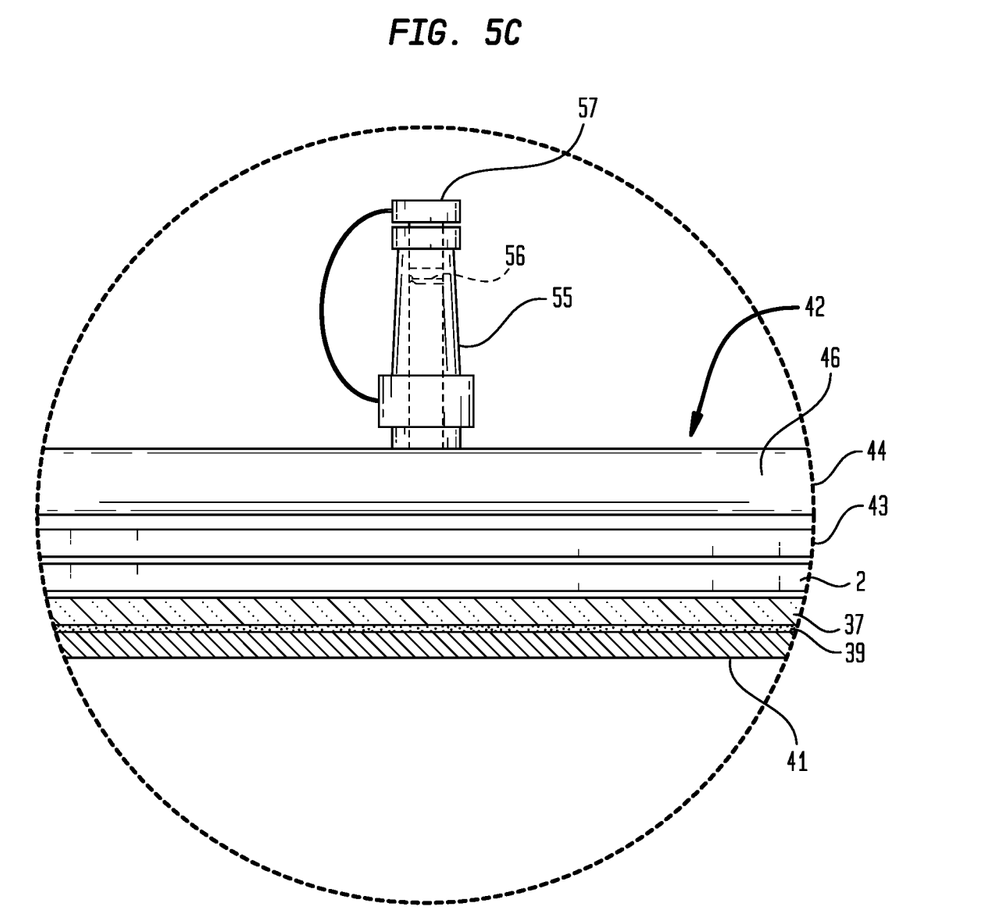
FIG. 5C is an enlargement of a portion of the surgical drape depicted in FIG. 5A.
Figure 5D:
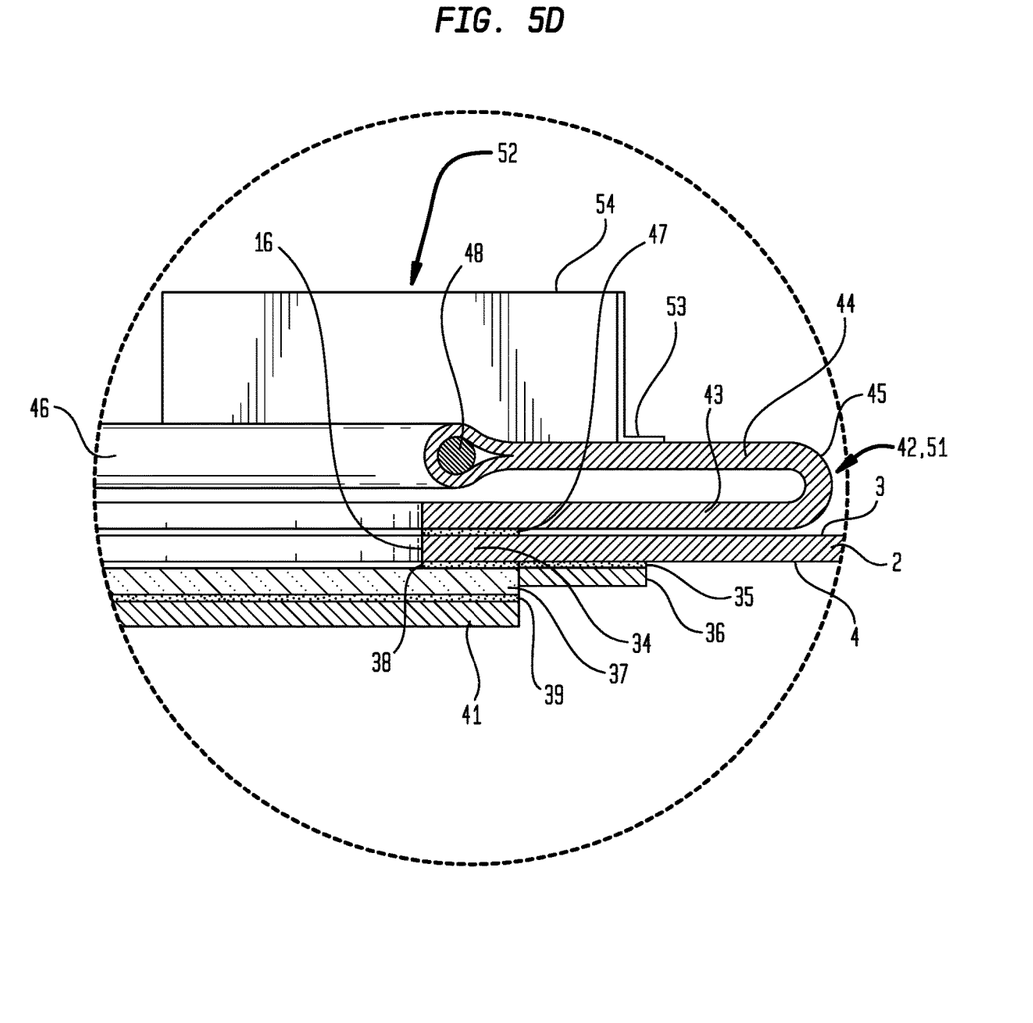
FIG. 5D is an enlargement of a portion of the surgical drape depicted in FIG. 5A.
Figure 5E:
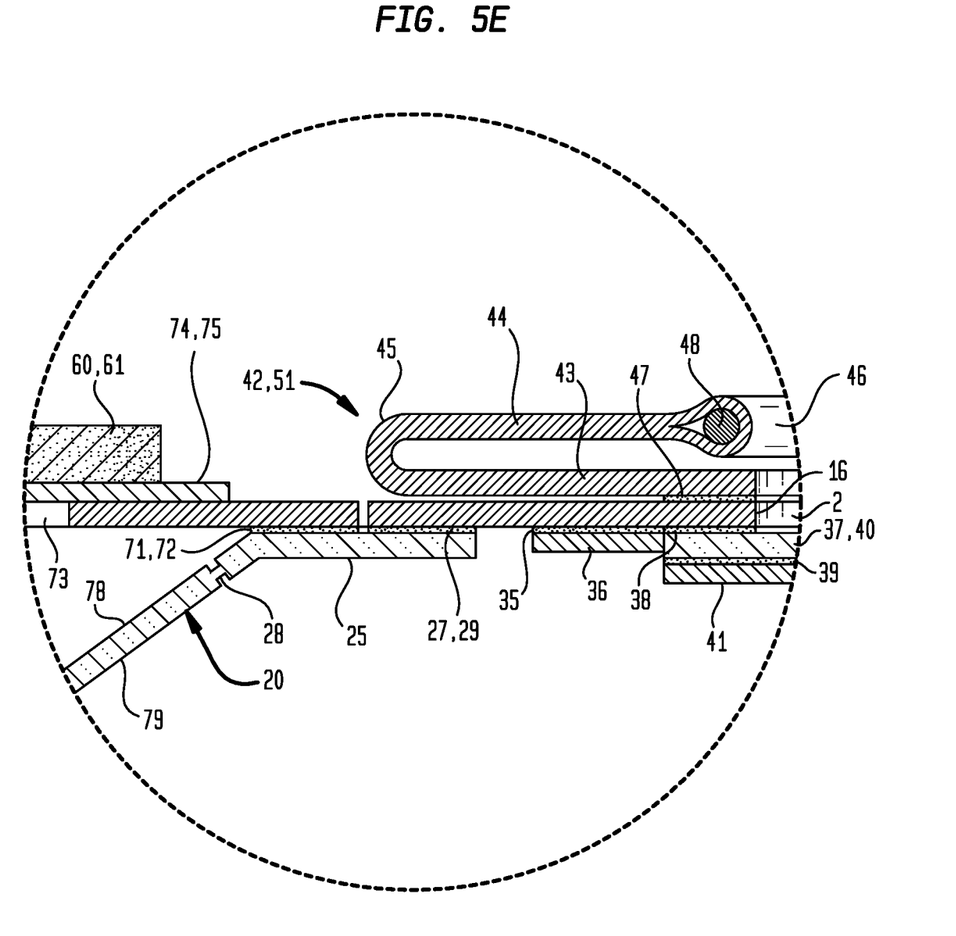
FIG. 5E is an enlargement of a portion of the surgical drape depicted in FIG. 5A.
Figure 6:
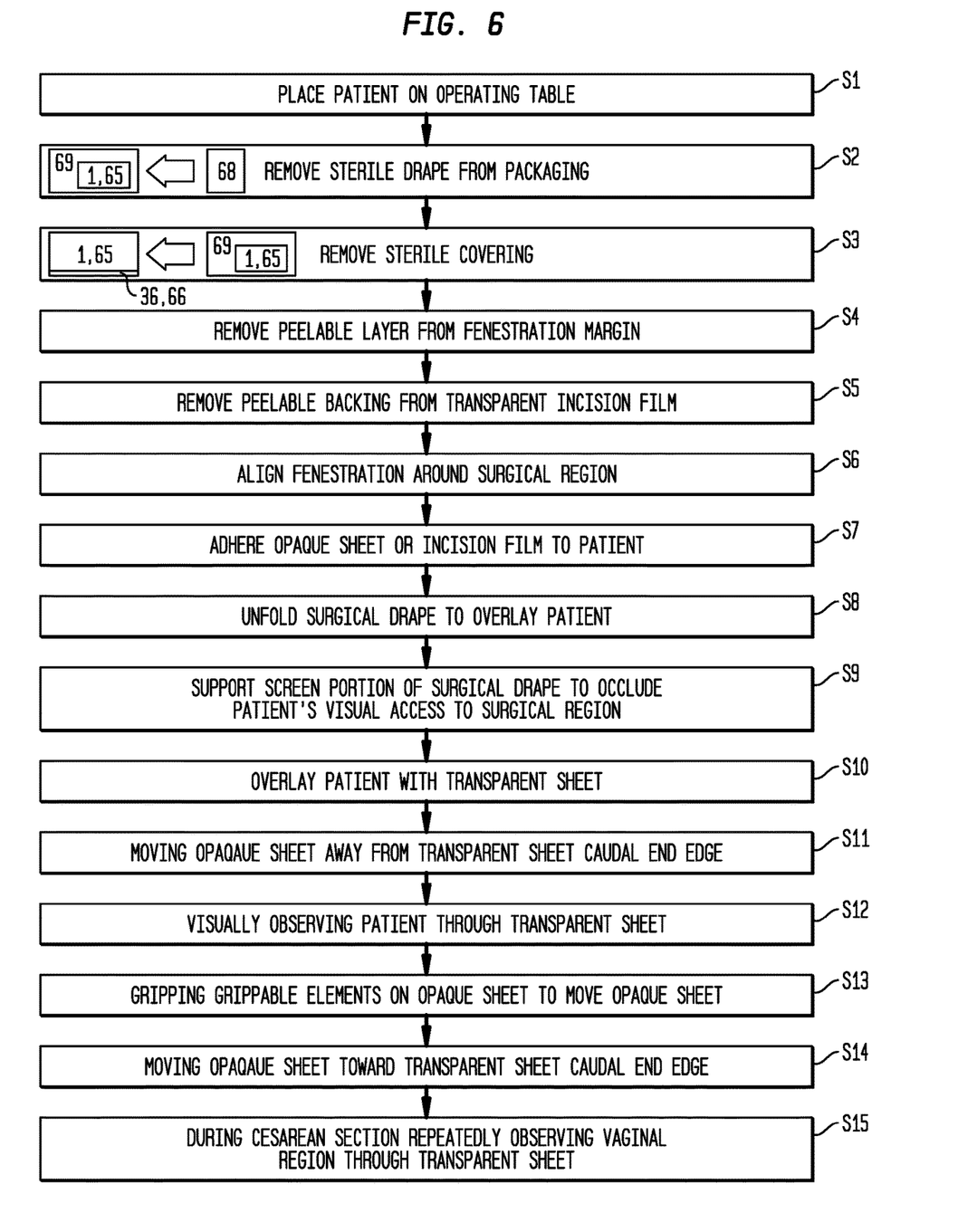
FIG. 6 is a block flow diagram of a method of using embodiments of the inventive surgical drape.

After the surgical procedure has begun, which can, but need not necessarily be, a cesarean section as illustrated in the Figures, the surgeon, at any time before, during or after the surgical procedure, including during a cesarean section delivery of an infant, further perform one or more of: moving the inferior region (19) of the opaque sheet (2) away from the transparent sheet (20)(block S11). Visually observing the patient (11) through the transparent sheet (20) from about the patient's waist (12) to the patient's feet (14) which during cesarean section can comprise visually observing the vaginal region (70) for evidence of obstetrical hemorrhage and commencing medical intervention, if indicated (block S12). In particular embodiments, the method can further include gripping grippable elements (31) disposed proximate the opaque sheet caudle end (7) and moving the opaque sheet caudal edge (7) toward the inferior aspect of the fenestration (16) to allow visualization of the patient through the transparent sheet (20) (block S13). When visualization is no longer needed, the method can further include one or more of: moving the inferior region (19) of the opaque sheet (2) toward the transparent sheet second end edge (24) in part or to the original position (S14). The method can further include repeatedly moving the inferior region (19) of the opaque sheet (2) toward the inferior aspect of the fenestration (16) and corresponding repeatedly visualizing the patient from the patient's waist (12) to the patient's feet (14), and during cesarean section repeatedly visualizing the vaginal region (70), due to the risk of obstetrical hemorrhage at any point during a cesarean section (block S15). The method generally allows for repeatedly visualizing the patient (11) from the patient's waist (12) to the patient's feet (14) while maintaining a sterile field.

As can be easily understood from the foregoing, the basic concepts of the present invention may be embodied in a variety of ways. The invention involves numerous and varied embodiments of a surgical drape and methods for making and using such surgical drape including the best mode.

As such, the particular embodiments or elements of the invention disclosed by the description or shown in the figures or tables accompanying this application are not intended to be limiting, but rather illustrative of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "drape" should be understood to encompass disclosure of the act of "draping"—whether explicitly discussed or not—and, conversely, were there effectively disclosure of the act of "draping", such a disclosure should be understood to encompass disclosure of a "drape" and even a "means for draping." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in Merriam-Webster's Collegiate Dictionary, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the surgical drapes herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A surgical drape, comprising:
   an opaque sheet having a surgeon facing side and a patient facing side extending to opposite opaque sheet side edges and opposite opaque sheet ends; and
   a transparent sheet joined medially between said opaque sheet ends by a peripheral margin to said patient facing side of said opaque sheet, wherein said opaque sheet include an opaque sheet overlay region;
   wherein said opaque sheet includes an opaque sheet overlay region;
   wherein said transparent sheet includes a transparent sheet overlay region;
   wherein said opaque sheet overlay region superimposes upon said transparent sheet overlay region; and
   wherein said opaque sheet overlay region movable relative to said transparent sheet overlay region.

2. The surgical drape of claim 1, further comprising a fenestration disposed in said opaque sheet to allow a surgeon access to a surgical region of a patient, said transparent sheet joined by said peripheral margin to said patient facing side of said opaque sheet proximate said fenestration.

3. The surgical drape of claim 2, further comprising a screen portion extending from said cephalad end, said screen portion configured to occlude patient's visual access to said surgical region when said opaque sheet overlays said patient.

4. The surgical drape of claim 2, further comprising one or more grippable elements coupled to said surgeon facing side of said opaque sheet, said one or more grippable elements disposed medially between opposite opaque sheet side edges proximate said caudal end of said opaque sheet.

5. The surgical drape of claim 2, further comprising an adhesive layer disposed about said fenestration on said patient facing side of said opaque sheet, said adhesive layer adapted to adhere to said patient to locate said surgical region within said fenestration.

6. The surgical drape of claim 5, further comprising a transparent incision panel joined to said opaque sheet over said fenestration.

7. The surgical drape of claim 6, further comprising an adhesive layer disposed on said patient facing side of said transparent incision panel said adhesion layer adapted to adhere to said patient to locate said transparent incision panel over said surgical region.

8. The surgical drape of claim 7, further comprising a peelable layer disposed over said adhesive layer of said transparent incision panel or said adhesive layer disposed about said fenestration, said peelable layer peelable to expose said adhesion layer or said adhesive layer.

9. The surgical drape of claim 2, further comprising an absorbent pad coupled medially to said surgeon facing side of said opaque sheet between said opaque sheet first and second side edges and proximate said fenestration.

10. The surgical drape of claim 1, further comprising one or more anchors coupled to said surgeon facing side of said opaque sheet.

* * * * *

UNITED STATES PATENT AND TRADEMARK OFFICE
CERTIFICATE OF CORRECTION

| | |
|---|---|
| PATENT NO. | : 11,944,404 B2 |
| APPLICATION NO. | : 17/837938 |
| DATED | : April 2, 2024 |
| INVENTOR(S) | : Javier Aguirre |

It is certified that error appears in the above-identified patent and that said Letters Patent is hereby corrected as shown below:

In the Claims

In Column 10, Line 13 (Claim 1, Line 7) following "said patient facing side of said opaque sheet" please delete ", wherein said opaque sheet includes an opaque sheet overlay region".

Signed and Sealed this
Tenth Day of December, 2024

Katherine Kelly Vidal
*Director of the United States Patent and Trademark Office*